United States Patent [19]
Lam

[11] 4,194,029
[45] Mar. 18, 1980

[54] NOVEL 4-CHROMANONE-7-PHOSPHATES AND PHOSPHONATES AND THE INSECTICIDAL USE THEREOF

[75] Inventor: Hsiao-Ling Lam, El Cerrito, Calif.

[73] Assignee: Stauffer Chemical Company, Westport, Conn.

[21] Appl. No.: 934,436

[22] Filed: Aug. 17, 1978

[51] Int. Cl.² .................. A61K 31/35; C07D 311/22
[52] U.S. Cl. ............................ 424/283; 260/345.2; 260/345.5
[58] Field of Search .................. 260/345.2, 345.5; 424/283

[56] References Cited
U.S. PATENT DOCUMENTS 3,453,291  7/1969  Jackim et al. .................. 260/345.2

Primary Examiner—Nicky Chan
Attorney, Agent, or Firm—Joel G. Ackerman

[57] ABSTRACT

Novel insecticidal and/or miticidal compounds have the formula

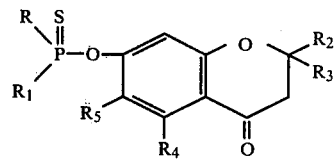

in which R is $C_1$–$C_3$ alkyl or $C_1$–$C_3$ alkoxy; $R_1$ is $C_1$–$C_3$ alkoxy; $R_2$ and $R_3$ are $C_1$–$C_3$ alkyl; $R_4$ is hydrogen or $C_1$–$C_3$ alkyl and $R_5$ is hydrogen, chloro or $C_1$–$C_3$ alkoxy.

16 Claims, No Drawings

NOVEL 4-CHROMANONE-7-PHOSPHATES AND PHOSPHONATES AND THE INSECTICIDAL USE THEREOF

This invention relates to novel compounds having the formula

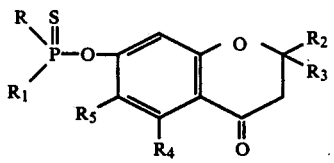

in which R is $C_1$-$C_3$ alkyl or $C_1$-$C_3$ alkoxy; $R_1$ is $C_1$-$C_3$ alkoxy; $R_2$ and $R_3$ are $C_1$-$C_3$ alkyl; $R_4$ is hydrogen or $C_1$-$C_3$ alkyl; and $R_5$ is hydrogen, chloro or $C_1$-$C_3$ alkoxy. $R_2$ and $R_3$ may be the same or different alkyl groups. The compounds of this invention have shown activity as insecticides and/or as miticides.

In one embodiment, R is $C_1$-$C_3$ alkyl and the compounds are phosphonates. In another embodiment, R is $C_1$-$C_3$ alkoxy and the compounds are phosphates.

Another aspect of this invention relates to a method of controlling or combatting insects or mites by applying an insecticidally or miticidally effective amount of a compound as defined herein to the insects or the mites or the locus thereof.

In still another aspect, this invention relates to insecticidal or miticidal compositions of matter comprising an insecticidally or miticidally effective amount of a compound as defined herein, with an inert carrier or diluent.

The novel compounds of this invention can be prepared by reaction of the appropriate chlorothiophosphate or phosphonate with the appropriate 7-hydroxy-4-chlomanone compound by the reaction:

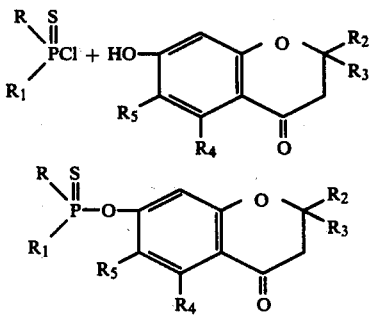

in the presence of potassium tertiary-butoxide and preferably using a solvent such as tetrahydrofuran, under reflux. The reaction temperature depends on the boiling point of the solvent and will generally be in the range of 20°–65° C.

The intermediate 7-hydroxy-4-chromanone compounds can be synthesized, for example, by the method described in Bhat, et al., tetrahedron 19, 77–83 (1963), using appropriate materials, or by reaction of a resorcinol or a substituted resorcinol with, for instance, 3,3-dimethylacrylic acid in the presence of a ring condensing agent, for instance, polyphosphoric acid.

The following are representative examples of preparation of compounds of this invention.

EXAMPLE 1

Preparation of 2,2-dimethyl-7-O,O-diethylthiophosphoro-4-chromanone (Compound 2 herein)

In a flask were placed 55.1 grams (0.5 mole) of resorcinol and 55.1 grams (0.5 mole) 3,3-dimethylacrylic acid. Then, 150 grams of polyphosphoric acid was added, and a steam bath applied to the flask. A red liquid began to form; the temperature of the reaction mixture quickly rose to 120° C. The flask was stirred for 45 minutes at 110° C., then allowed to cool. The contents were poured into a mixture of 500 milliliters water and 400 milliliters methylene chloride then stirred and filtered. The precipitate was washed several times with portions of methylene chloride, water and toluene. There was obtained 65.8 grams, (68% of theoretical yield) 2,2-dimethyl-7-hydroxy-4-chromanone, m.p. 170°–174° C.

In a flask was placed 1.92 grams (0.01 mole) of 2,2-dimethyl-7-hydroxy-4-chromanone and 100 milliliters of tetrahydrofuran; then 1.12 grams (0.01 mole) potassium tertiary-butoxide was added. The mixture was refluxed for one-half hour at which time the flask contained a clear yellow solution with a brown paste which had formed on the bottom. The materials in the flask were cooled and a solution of 1.88 grams (0.01 mole) of diethyl chlorothiophosphate in 10 milliliters of tetrahydrofuran was added. The clear yellow solution became cloudy. The mixture was stirred for one hour at room temperature and refluxed for two hours, then stripped to remove solvent. The remaining materials were extracted with methylene chloride; the extract was washed twice with water and once with brine and dried over magnesium sulfate. On stripping, there was obtained 3.07 grams (89% of theoretical) of the desired product, $n_D^{30}$ 1.5335. The structure of the compound was confirmed by IR (infrared) and NMR (nuclear magnetic resonance) analyses.

EXAMPLE 2

Preparation of 2,2-dimethyl(6-chloro-7-O-ethyl,ethylthiophosphonyl-4chromanone (Compound 5 herein)

In 50 milliliters of tetrahydrofuran there was dissolved 1.112 grams (0.01 mole) of potassium tertiary-butoxide. There was then added drop-wise a solution of 2.26 grams (0.01 mole) of 6-chloro-7-hydroxy-4-chromanone dissolved in 50 milliliters of tetrahydrofuran. The mixture was refluxed one half hour, then cooled in an ice bath. Following this, a solution of 1.72 grams (0.01 mole) O-ethyl, ethyl chlorothiophosphonate in 20 milliliters of tetrahydrofuran was added over a period of one hour. The mixture was stirred at room temperature for two hours, then refluxed for two additional hours. The solvent was stripped and the residue extracted with 100 milliliters of methylene chloride and washed twice with water. The organic layer was separated and washed with 300 milliliters of brine, then dried over magnesium sulfate. The product was then stripped to remove solvent. There was obtained 2.31 grams (64% of theoretical) of the desired product, $n_D^{30}$ 1.5510. The structure of the compound was confirmed by IR and NMR analyses.

The following Table 1 contains some representative insecticidal compounds of this invention:

TABLE I $$\underset{R_1}{\overset{R}{P}}-O-\underset{R_5}{\overset{S}{\underset{R_4}{\bigcirc}}}-O-\underset{O}{\overset{R_2}{\underset{R_3}{\bigcirc}}}$$

| Compound No. | R | $R_1$ | $R_2$ | $R_3$ | $R_4$ | $R_5$ | $n_D^{30}$ or m.p. |
|---|---|---|---|---|---|---|---|
| 1 | $C_2H_5$ | $C_2H_5O$ | $CH_3$ | $CH_3$ | H | H | 1.5438 |
| 2 | $C_2H_5O$ | $C_2H_5O$ | $CH_3$ | $CH_3$ | H | H | 1.5335 |
| 3 | $CH_3O$ | $CH_3O$ | $CH_3$ | $CH_3$ | H | H | 1.5465 |
| 4 | $C_2H_5$ | $C_2H_5O$ | $CH_3$ | $CH_3$ | H | $OCH_3$ | 1.5411 |
| 5 | $C_2H_5$ | $C_2H_5O$ | $CH_3$ | $CH_3$ | H | Cl | 1.5510 |
| 6 | $n\text{-}C_3H_7O$ | $n\text{-}C_3H_7O$ | $CH_3$ | $CH_3$ | H | H | 1.5227 |
| 7 | $C_2H_5$ | $C_2H_5O$ | $CH_3$ | $CH_3$ | $CH_3$ | H | 1.5455 |

The structure of these compounds was variously confirmed by infrared (ir) and nuclear magnetic resonance (nmr) spectral analysis.

INSECTICIDAL EVALUATION

The compounds in the above Table 1 were tested for insecticidal activity. The following testing procedures were used.

Housefly [*Musca domestica* (Linn.)]: Test compounds were diluted in acetone and aliquots pipetted onto the bottom of 55×15 millimeter aluminum dishes. To insure even spreading of the chemical on the bottom of the dishes, 1 milliliter of acetone containing 0.02% peanut oil was also added to each dish. After all solvents had evaporated, the dishes were placed in circular cardboard cages containing 25 female houseflies, one to two days old. The cages were covered on the bottom with cellophane and on top with tulle netting, and each contained a sugar-water saturated cotton plug for maintenance of the flies. Mortality was recorded after 48 hours. Test levels ranged from 100 μg/25 female houseflies down to that at which approximately 50% mortality occurred. The LD-50 values are expressed below in Table II under the heading "HF", in terms of μg of the test compound per 25 female flies.

German Cockroach [*Blatella germanica* (Linn.)]: Test compounds were diluted in a 50—50 acetone-water solution. 2 cc. of the solution were sprayed through a hand spray gun into circular cardboard cages containing 10 one-month-old German cockroach nymphs. The test cages were covered on the bottom with cellophane and on the top with tulle netting. Percent mortality was recorded 4 days later. Test concentrations ranged from 0.1% down to that at which approximately 50% mortality occurred. LD-50 values are expressed below in Table II under the heading "GR", in terms of percent of the test compound in the sprayed solution.

Lygus Bug [*Lygus hesperus* (Knight)]: Test compounds were diluted in a 50—50 acetone-water solution. 2 cc. of the solution were sprayed through a hand spray gun into circular cardboard cages containing 1 string bean pod and 10 adult lygus bugs. The test cages were covered on the bottom with cellophane and on the top with tulle netting. Percent mortality was recorded 48 hours later. Test concentrations ranged from 0.05% down to that at which approximately 50% mortality occurred. LD-50 values are expressed below in Table II under the heading "LB" in terms of percent of the test compound in the sprayed solution.

Black Bean Aphid [*Aphis fabae* (Scop.)]: Nasturtium plants (Tropaeolum Sp.) approximately 5 cm. tall, were transplanted into sandy loam soil in 3-inch clay pots and infested with 25-50 black bean aphids of mixed ages. 24 hours later, they were sprayed, to the point of runoff, with 50—50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table II under the heading "BA" in terms of percent of the test compound in the sprayed solutions.

Green Peach Aphid [*Myzus persicae* (Sulzer)]: Radish plants (Rhaphanus sativus), approximately 2 cm. tall, were transplanted into sandy loam soil in 3-inch clay pots and infested with 25-50 green peach aphids of mixed ages. 24 hours later, they were sprayed, to the point of runoff, with 50—50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table II under the heading "GPA" in terms of percent of the test compound in the sprayed solution.

Saltmarsh caterpillar (*Estigmene acrea* (Drury)]: Test compounds were diluted in a 50—50 acetone-water solution. Sections of curly dock (*Rumex crispus*) leaves, approximately 1×1.5 inches, were immersed in the test solution for 2-3 seconds and placed on a wire screen to dry. The dried leaves were placed in petri dishes containing a moistened piece of filter paper and infested with 5 second-instar saltmarsh larvae. Mortality of the larvae was recorded 48 hours later, and a piece of synthetic media was added to dishes containing survivors. These were then held for 5 additional days to observe for any delayed effects of the test chemicals.

Test concentrations ranged from 0.05% down to that at which approximately 50% mortality occurred. LD-50 values are expressed below in Table II under the heading "SMC", in terms of percent of the test compound in the solution.

Cabbage Looper [(*Trichoplusia ni* (Hubner)]: Test compounds were diluted in a 50—50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with five second-instar cabbage looper larvae. Mortality of the larvae was recorded 48 hours later, and a piece of synthetic media added to dishes containing survivors. These were then held for five additional days to observe for any delayed effects of the test chemicals.

Test concentrations ranged from 0.05% to that at which approximately 50% mortality occurred. LD-50 values are expressed below in Table II under the heading "CL" in terms of percent of the test compound in this solution.

Tobacco budworm [*Heliothis virescens* (Fabricus)]: Test compounds were diluted in a 50—50 acetone-water solution. Sections of Romaine lettuce (*Latuca sativa*) leaves, approximately 1×1.5 inches, were immersed in the test solutions for 2-3 seconds and placed on a wire screen to dry. The dried leaves were placed in petri dishes containing a moistened piece of filter paper and infested with five second-instar tobacco budworm larvae. Mortality of the larvae was recorded 48 hours later, and a piece of synthetic media added to dishes containing survivors. These were then held for five additional days to observe for any delayed effects of the test chemicals.

Test concentrations ranged from 0.1% to that at which approximately 50% mortality occurred. LD-50 values are expressed below in Table II under the heading "TBW" in terms of percent of the test compound in the solution.

Southern House Mosquito Larvae [*Culex pipiens quinquefasciatus* (Say)]: Insecticidal activity was determined using third-instar larvae of the mosquito *Culex pipiens quinquefasciatus*. Ten larvae were placed in a six-ounce cup containing 100 ml. of an aqueous solution of the test chemical. The treated larvae were stored at 70° F. and 48 hours later the mortality recorded. Test concentrations ranged from 0.5 ppm down to that at which approximately 50% mortality occurs. LD-50 values are expressed below in Table II under the heading "MOS" in terms of percent of the test compound in the solution.

MITICIDAL EVALUATION

The compounds in Table 1 were tested for miticidal activity utilizing the two-spotted mite (2-SM), *Tetranychus urticae* (Koch). The test procedure was as follows:

Pinto bean plants (Phaseolus sp.) approximately 10 cm. tall, were transplanted into sandy loam soil in 3-inch clay pots and thoroughly infested with two-spotted mites of mixed ages and sexes. 24 hours later, the infested plants were inverted and dipped for 2-3 seconds in a 50—50 acetone-water solution of the test chemicals. Treated plants were held in the greenhouse, and 7 days later mortality was determined for both the adult mites and the nymphs hatching from eggs which were on the plants at the time of treatment. Test concentrations ranged from 0.05% down to that at which 50% mortality occurred. LD-50 values are expressed below in Table II under the headings "2SM-PE" (i.e., post-embryonic) and "2SM-Eggs", in terms of percent concentration of the test compound in the solution.

TABLE II

| Compound No. | HF, μg | BA, % | GPA, % | GR, % | LB, % | SMC, % | CL, % | TBW, % | MOS, ppm | 2-SM PE, % | 2-SM EGGS, % |
|---|---|---|---|---|---|---|---|---|---|---|---|
| 1 | 4 | 0.01 | 0.03 | >0.1 | 0.008 | >0.03 | >0.05 | 0.03 | 0.008 | 0.05 | >0.05 |
| 2 | 10 | >0.05 | — | >0.1 | >0.05 | >0.05 | >0.05 | 0.05 | 0.02 | >0.05 | >0.05 |
| 3 | >10* | 0.03 | 0.03 | — | — | — | — | 0.05 | 0.08 | >0.05 | >0.05 |
| 4 | 8.5 | 0.004 | 0.005 | 0.02 | 0.008 | — | >0.05 | 0.03 | 0.02 | >0.05 | >0.05 |
| 5 | >10* | >0.05 | — | — | — | — | — | 0.05 | 0.8 | 0.05 | >0.05 |
| 6 | >10* | >0.05 | — | — | — | — | — | 0.05 | 0.3 | >0.05 | >0.05 |
| 7 | 4 | 0.007 | — | <0.1 | <0.05 | — | <0.1 | 0.02 | — | 0.002 | 0.006 |

*LD-50 less than 100, but greater than 10 μg/25 female flies.

The compounds of this invention are generally embodied into a form suitable for convenient application. For example, the compounds can be embodied into pesticidal compositions which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite, diatomite; gypsum; clays, propellants, such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal composition of this invention are used in any particular instances will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise between about 0.01 and about 90% by weight of the composition.

What is claimed is:

1. A compound having the formula

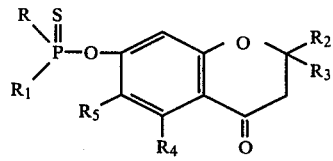

in which R is $C_1$–$C_3$ alkyl or $C_1$–$C_3$ alkoxy, $R_1$ is $C_1$–$C_3$ alkoxy, $R_2$ and $R_3$ are $C_1$–$C_3$ alkyl; $R_4$ is hydrogen or $C_1$–$C_3$ alkyl; and $R_5$ is hydrogen, chloro or $C_1$–$C_3$ alkoxy.

2. A compound according to claim 1 in which R is $C_1$–$C_3$ alkyl.

3. A compound according to claim 1 in which R is $C_1$–$C_3$ alkoxy.

4. A compound according to claim 1 in which $R_2$ and $R_3$ are both methyl.

5. A compound according to claim 1 in which R is ethyl, $R_1$ is ethoxy, $R_2$ and $R_3$ are both methyl, and $R_4$ and $R_5$ are hydrogen.

6. A compound according to claim 1 in which R and $R_1$ are both ethoxy, $R_2$ and $R_3$ are both methyl and $R_4$ and $R_5$ are both hydrogen.

7. A compound according to claim 1 in which R and $R_1$ are both methoxy, $R_2$ and $R_3$ are both methyl and $R_4$ and $R_5$ are both hydrogen.

8. A compound according to claim 1 in which R is ethyl, $R_1$ is ethoxy, $R_2$ and $R_3$ are both methyl, $R_4$ is hydrogen and $R_5$ is methoxy.

9. A compound according to claim 1 in which R is ethyl, $R_1$ is ethoxy, $R_2$ and $R_3$ are both methyl, $R_4$ is hydrogen and $R_5$ is chloro.

10. A compound according to claim 1 in which R and $R_1$ are both n-propoxy, $R_2$ and $R_3$ are both methyl and $R_4$ and $R_5$ are both hydrogen.

11. A compound according to claim 1 in which R is ethyl, $R_1$ is ethoxy, $R_2$ and $R_3$ are both methyl, $R_4$ is methyl and $R_5$ is hydrogen.

12. A method of controlling insects or mites comprising applying to the insects or mites or the locus thereof an insecticidally or miticidally effective amount of a compound having the formula

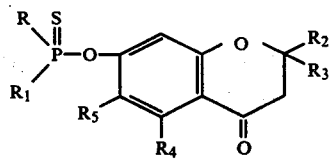

in which R is $C_1$–$C_3$ or $C_1$–$C_3$ alkoxy; $R_1$ is $C_1$–$C_3$ alkoxy; $R_2$ and $R_3$ are $C_1$–$C_3$ alkyl; $R_4$ is hydrogen or $C_1$–$C_3$ alkyl and $R_5$ is hydrogen, chloro or $C_1$–$C_3$ alkoxy.

13. A method according to claim 12 in which R is $C_1$–$C_3$ alkyl.

14. A method according to claim 12 in which R is $C_1$–$C_3$ alkoxy.

15. A method according to claim 12 in which $R_2$ and $R_3$ are both methyl.

16. An insecticidal or miticidal composition of matter comprising:
(a) an insecticidally or miticidally effective amount of a compound having the formula

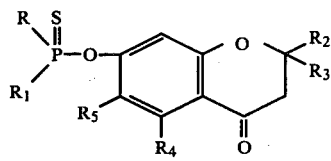

in which R is $C_1$–$C_3$ alkyl or $C_1$–$C_3$ alkoxy; $R_1$ is $C_1$–$C_3$ alkoxy; $R_2$ and $R_3$ are $C_1$–$C_3$ alkyl; $R_4$ is hydrogen or $C_1$–$C_3$ alkyl and $R_5$ is hydrogen, chloro or $C_1$–$C_3$ alkoxy; and
(b) an inert carrier or diluent.

* * * * *